United States Patent [19]
Inbar et al.

[11] 3,971,952
[45] July 27, 1976

[54] METHOD OF DETECTING ABNORMAL BEHAVIOR OF MAMMALIAN CELLS

[75] Inventors: Michael Inbar; Meir Shinitzky, both of Rehovoth, Israel

[73] Assignee: Yeda Research & Development Co. Ltd., Rehovoth, Israel

[22] Filed: Sept. 12, 1974

[21] Appl. No.: 505,530

[30] Foreign Application Priority Data
Sept. 14, 1973 Israel.................................... 43224

[52] U.S. Cl................................ 250/461 B; 250/302
[51] Int. Cl.²........................................ G01N 21/38
[58] Field of Search.......... 250/302, 458, 461, 461 B

[56] References Cited
UNITED STATES PATENTS 3,854,050  12/1974  Peterson et al.................. 250/461 X
3,857,033  12/1974  Cobb................................. 250/302
3,864,571  2/1975   Stillman et al..................... 250/302

*Primary Examiner*—Archie R. Borchelt
*Attorney, Agent, or Firm*—Browdy and Neimark

[57] ABSTRACT

Abnormal behavior of mammalian cells is detected in vitro by measuring the fluidity or an associated phenomenon of the lipid layer of the cell surface membrane. Abnormal behavior of cells, in particular if caused by malignant transformations, is associated with increase of fluidity of the liquid layer of the cell membrane, as compared with normal cells. The fluidity can be determined, e.g., by measuring the degree of fluorescence polarization of the radiation emitted from a suspension of cells labelled in the lipid layer with a fluorescent compound. 1,6-Diphenyl-1,3,5-hexatriene was found to be a suitable fluorescent probe.

8 Claims, 1 Drawing Figure

U.S. Patent   July 27, 1976   3,971,952
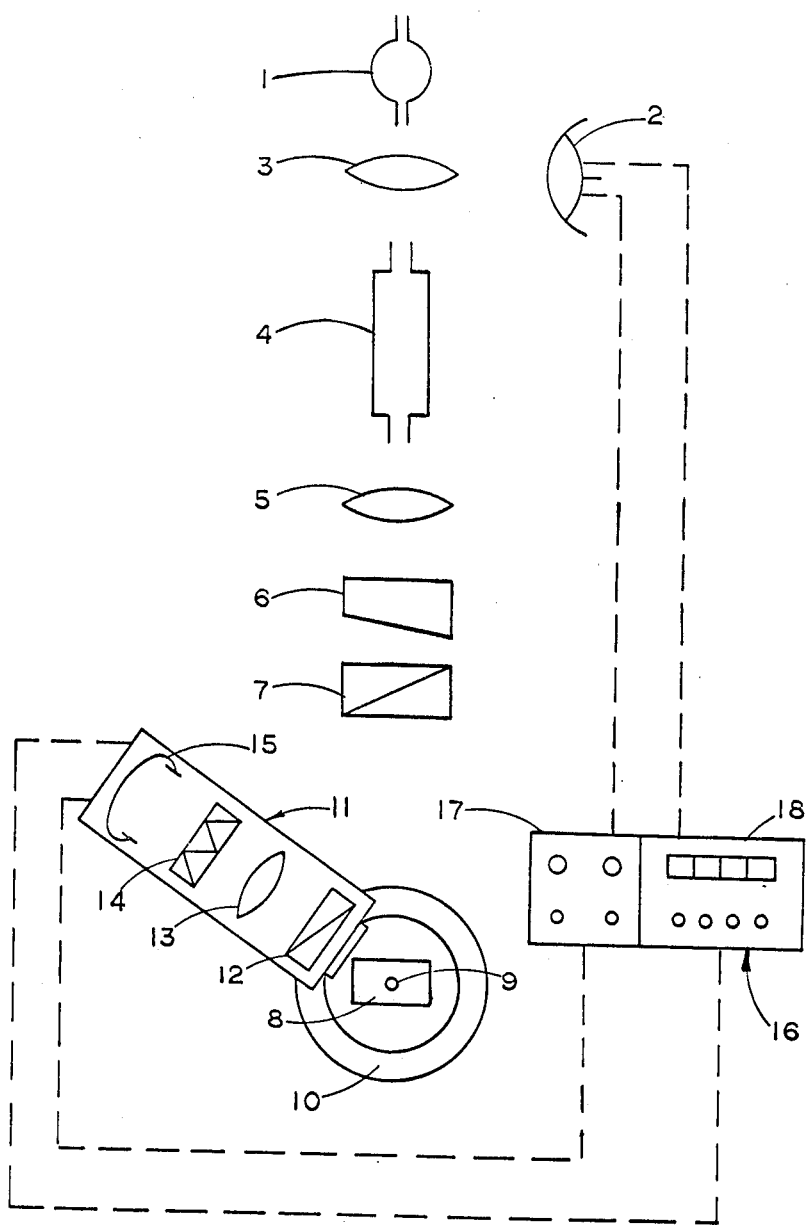

METHOD OF DETECTING ABNORMAL BEHAVIOR OF MAMMALIAN CELLS

This invention concerns a method of detecting in vitro abnormal behaviour of mammalian cells, in particular changes in the fluid state of the lipid layer of cell surface membranes which are associated with malignant transformations of normal cells. The invention thereby provides a diagnostic tool for detecting the occurrence of tumors in mammals.

The dynamics of cell-surface membranes, in particular the freedom of membrane components to undergo thermal motion, commonly termed "membrane fluidity," is currently believed to play an important role in cellular regulatory mechanisms. The dynamic properties of cell surface membranes are mainly determined by the fluidity of its lipid layer. The fluidity of the lipid layer may be expressed in terms of the microviscosity of that layer, a term that was introduced by Shinitzky et al. (Biochemistry, 10, 2106–2113 (1971)) in connection with fluorescence polarization studies on the hydrocarbon region of synthetic micelles. Similar studies were later conducted on the fluidic properties of liposomes (Cogan et al., Biochemistry, 12, 521–528 (1973)) and on isolated biological membranes ("ghosts") (Rudy and Gitler, Biochim, Biophys. Acta 288, 231–236 (1972)). The techniques used in all the aforesaid studies were based on fluorescence polarization measurements of a fluorescent probe embedded in the analyzed region. The fluidity properties of the lipid layer of cell membranes can, however, be determined, in terms of microviscosity or other associated parameters, by means of other physical methods, such as NMR or ESR, (see e.g., E. Oldfield and D. Chapman, Fed. Eur. Biochem. Soc. Lett. 21, 303–306 (1972); M. T. Flanagan and T. R. Hesketh, Biochim. Biophys. Acta 298, 535–545 (1973); W. L. Hubbell and H. M. McConnell, J. Amer. Chem. Soc. 93, 314–326 (1971); and the reviews by H. M. McConnell and B. Gaffney in Quater. Rev. Biophys. 3, 91–136 (1970) and by C. Gitler in Annu. Rev. Biophys. Bioeng. 1, 51–92 (1972)).

It has now been found, in accordance with the present invention, that abnormal behaviour of mammalian cells, in particular such as is caused by malignant transformation, is associated with marked changes in the fluidity of the lipid layer of the surface membrane of the cells. The lipid layer of abnormal cells was found to be more fluid than that of normal cells of the same type. It has been found, for example, that the microviscosity of the lipid layer of the surface membrane of malignant lymphoma cells from mice is almost half that of normal lymphocites from the same strain of mice. Similar results were obtained with lymphatic leukemia cells from human patients suffering from chronic lymphatic leukaemia or acute lymphoblastic leukaemia.

The invention thus provides a method of detecting abnormal behaviour of mammalian cells, which comprises measuring the fluidity, or an associated phenomenon, of the lipid layer of the cell surface membrane and comparing the measurement thereby obtained with that of normal cells of the same type.

As indicated above the fluidity of the lipid layer of the cell surface membrane can be determined by measuring a phenomenon associated therewith, or dependent thereon, by any suitable physical method, such as, e.g., fluorescence polarization analysis, NMR and ESR. Such a measurement may involve the observation of an electromagnetic signal which is specific to certain atoms, groups of atoms or molecules which are natural components of the lipid layers. Alternatively, there might be signals originating from suitable so-called "probes" i.e., suitable label molecules selectively introduced into the hydrocarbon region of the lipid layer. The measured values of the observed fluidity-associated phenomena, may be translated into terms of microviscosity or its reciprocal, fluidity, but the measured values might also be used as such for the comparison with the corresponding values obtained from measurements on other cells.

In accordance with one embodiment of the invention, the fluidity of the lipid layer of the surface membrane of mammalian cells is determined by the fluorescence polarization analysis of a fluorescent probe embedded in the lipid layer. In accordance with this method, which is based on the technique described by Shinitzky et al. (Biochemistry 10, 2106–2113 (1971)) a suspension of the cells, the membrane lipid layer of which having been stained with a suitable fluorescent probe, is exposed to a plane-polarized excitation radiation at a suitable wavelength, and the intensities of the fluorescent emission of the sample is measured after being passed through a polarizer oriented, respectively, parallel and perpendicular to the direction of polarization of the excitation radiation, or simultaneously through a pair of polarizers oriented parallel and perpendicular, respectively, to that direction. The measured intensities relate to the degree of fluorescent polarization, $P$, to the fluorescence anistropy $r$, and to the total fluorescence intensity $F$, by the following equations:

$$P = \frac{I_{\parallel} - I_{\perp}}{I_{\parallel} + I_{\perp}} = \frac{I_{\parallel}/I_{\perp} - 1}{I_{\parallel}/I_{\perp} + 1}$$

$$r = \frac{I_{\parallel} - I_{\perp}}{I_{\parallel} + 2I_{\perp}} = \frac{I_{\parallel}/I_{\perp} - 1}{I_{\parallel}/I_{\perp} + 2}$$

$$F = I_{\parallel} + 2I_{\perp} = I_{\perp}(I_{\parallel}/I_{\perp} + 2)$$

where $I_{\parallel}$ and $I_{\perp}$ are the fluorescence intensities detected through a polarizer oriented parallel and perpendicular, respectively, to the direction of polarization of the excitation beam.

The rotational depolarization of a fluorophore can be described by the Perrin equation:

$$\frac{r_o}{r} = 1 + C(r)\frac{T\tau}{\bar{\eta}}$$

where $r$ and $r_o$ are the measured and the limiting fluorescence anisotropies, $T$ is the absolute temperature, $\tau$ is the excited state lifetime and $\bar{\eta}$ is the microviscosity of the medium. $C(r)$ is a parameter that relates to the molecular shape of the fluorophor and has a specific value for each $r$. A calibration curve of $r_o/r$ versus $T\tau/\bar{\eta}$ can be obtained for each specific probe, according to previously described methods, and these curves can be used for the derivation of the microviscosity $\bar{\eta}$ with the aid of the determined $r$, $T$ and $\tau$ values.

As shown above, the fluorescence anisotropy $r$ is derived from the measured values of $I_{\parallel}/I_{\perp}$ and it follows from the definition of $r$ that it can be derived from a single measured parameter, namely the ratio $I_{\parallel}/I_{\perp}$. This ratio can be measured directly by the use of two detectors or by the use of a single detector and two alternating excitation beams polarized at right angles to each other.

The microviscosity obtained by this procedure represents the harmonic mean of the effective viscosities opposing the rotation of the probe molecule in all possible directions and is expressed in absolute macroscopic units, e.g., poise.

In practice it has been found that in order to detect abnormal behaviour of cells, in accordance with the invention, it is not necessary to convert the measured values of $I_{\|}$ and $I_{\perp}$ or $I_{\|}/I_{\perp}$ into values of microviscosity. The differentiation of abnormal cells from normal ones can be achieved with the same degree of reliability, by comparing the $I_{\|}/I_{\perp}$ ratios obtained from measurements of the tested cell sample with that obtained from normal cells. The obtained ratio $I_{\|}/I_{\perp}$ or the value of $r$ derived therefrom are absolute values at a known temperature and can serve as the criterion for abnormality. This will be shown in the Tables included in the Examples herein.

Fluorescent molecules suitable for use as probes in the above described fluorescence polarization technique, should preferably be of a pure hydrocarbon structure in order to be able to penetrate and remain embedded in the hydrocarbon region of the lipid layer. In accordance with the present invention it has been found that suitable probes for use in the above described fluorescence polarization technique are members of the group consisting of 1,6-diphenyl-1,3,5-hexatriene (hereinafter "DPH") and lower alkyl derivatives thereof. Particularly preferred is DPH, owing to its suitable spectral characteristics. This compound, which has not been used before as a probe in fluorescence studies, has an intense absorption maximum ($\epsilon \approx 80,000$ $M^{-1}cm^{-1}$) at about 350 nm and well-separated absorption and emission spectra, owing to which both the possibility of excitation energy transfer from one DPH molecule to another and the contribution of scattered excitation light to the fluorescent signal, are reduced. These two effects are of the main sources of errors in fluorescence polarization measurements and wee found to be negligible in DPH-labeled systems. The intense absorption maximum and the high fluorescence quantum yield (0.8 in hexane at 25°C) facilitate the detection of a fluorescence signal at concentrations as low as $10^{-8}M$. DPH in purified heavy liquid paraffin at a concentration of $2 \times 10^{-6}M$ at 25°C displays an excited state lifetime of $\tau = 10.5$ ns.

As could be expected from its hydrocarbon nature, DPH is practically insoluble in water. It has been found, however, that when a DPH solution in tetrahydrofuran is blown into a vigorously stirred aqueous medium, clear and stable dispersions of DPH, which are practically void of fluorescence, are obtained. It has further been found, in accordance with this invention, that when an aqueous cell suspension was mixed with about an equal volume of the aforesaid DPH dispersion and the mixture incubated at 25°C, DPH penetrated into the lipid layer of the cell surface membranes, as witnessed by a steep increase in the fluorescence intensity of the suspension, which levels off after about 60 minutes. It is estimated that one DPH molecule was incorporated into the lipid layer of the membranes per about 1000 lipid molecules.

The fluorescence signal of systems containing DPH was found to decrease with time of exposure to the excitation light. On shutting off the excitation light for periods of 15–30 seconds, the system retained its original fluorescence signal. This phenomenon presumably originates from reversible photoisomerizations of DPH from the all-transconfiguration to alternative configurations. In order to eliminate this effect, the measurements were conducted in periods not exceeding 10 seconds.

The fluorescence polarization measurements, in accordance with the above described embodiments of the invention, can be carried out with any suitable apparatus which comprises a source of polarized light radiation, preferably in the range of from 200 to 700 nm, at least one detection system comprising a polarizer and means for measuring the intensity of light passing through that polarizer. The apparatus should further comprise means for changing at will the mutual orientation of the polarizers so as to enable the measurement of the fluorescence intensities at a crossed and at a parallel direction to the direction of polarization of the exciting beam.

An accurate apparatus has been designed for this purpose and will be schematically described hereinbelow with reference to the enclosed drawing.

The drawing represents schematically an apparatus for carrying out accurate measurements of fluorescence polarization, wherein a beam of exciting light emitted by the light source 1 is passed through a quartz lens 3, a monochromator 4, a second collimating quartz lens 5, a wedge depolarizer 6 and a Glan-Thompson polarizer 7. The polarized ray of exciting light emanating from the polarizer 7 passes through a cylindrical quartz cuvette or test tube 9 containing the sample to be examined and located in a thermostat 8. A detector system 11 comprises a Glan-Thompson polarizer 12, a quartz lens 13, a cut-off filter 14 and a photomultiplier 15. The polarizer 12 is oriented so as to have its plane of polarization in a vertical direction (perpendicular to the plane of the paper of the drawing) and the entire detector assembly is mounted on a circular track 10 so as to be rotatable around the center of the sample cuvette 9, in order to permit the measurement of the fluorescent emission at different angles to the excitation beam. A photodiode compensator 2 is provided adjacent to the light source 1 and serves for correcting fluctuations of the light intensity of the source. The apparatus further comprises a control unit 16 including power supplies 17 for the photomultiplier 15 and for the photodiode 2 and a readout unit 18.

In operation the sample is placed in the sample cuvette 9 and the thermostat 8 is allowed to reach the desired temperature. The sample is exposed to excitation light from the light source 1, which may be, e.g., a mercury or a xenon-mercury arc. The excitation light from the source is focused by the lens 3 into a high intensity monochromator 4. The monochromatic beam is collimated by the lens 5 and passed through the double-wedge depolarizer 6 into the Glan-Thompson polarizer 7, which can be accurately adjusted at different orientations. The fluorescent emission from the excited sample passes through the vertically-oriented polarizer 12 and is focused by the lens 13 into the photomultiplier 15. The cut-off filter 14 serves to cut off any scattered excitation light and is chosen in accordance with the wavelength of the exciting light. The output signal of the photomultiplier 15 is fed to the control unit 16 wherein it is compared with the signal from the photodiode compensator 2. The compensated signal is amplified and can be read on the read-out unit 18 or recorded.

The depolarizer 6 serves to eliminate any polarization in the excitation radiation before it passes through the polarizer 7 so as to render the intensity of the polarized beam which excites the sample independent of the orientation of the polarizer 7. The depolarization device can be adjusted by rotation to a position at which the measured fluorescence intensity of a fully depolarized solution (e.g. $10^{-5}$M acridine hydrochloride in methanol) is the same when the excitation polarizer 7 is oriented vertically or horizontally (while the detecting polarizer 12 is oriented vertically). Once the depolarizer is so adjusted, deviations of less than 1 percent over the whole excitation range are attainable and, if desired, corrections for these deviations can be applied.

The intensity of the fluorescence is measured once with the excitation polarizer 7 oriented vertically, (i.e. with its direction of polarization parallel to the direction of polarization of the polarizer 12) to obtain the value of $I_\parallel$ and again when the excitation polarizer 7 is oriented horizontally to obtain the value of $I_\perp$.

In order to minimize or eliminate errors caused by scattered or stray light when the sample is a turbid solution or suspension, the detector assembly 11 is rotated along the track 10 to an angle at which the ratio of the fluorescence intensity to the stray light intensity is maximal, and measurements are taken at this angle. This optimal angle is determined with the aid of an unlabelled reference sample of equal turbidity which is void of fluorescence, with the excitation polarizer 7 and the detecting polarizer 12 being both vertically oriented. It is also possible to correct the $I_\perp$ and $I_\parallel$ measurements for the contribution of scattered light, using the readings obtained with the aforesaid reference solution.

Fluorescene polarization can also be measured with an instrument similar to that described by Weber and Bablouzian (J. Biol.Chem. 241, 2558 (1966)), wherein the excitation unit, which comprises components corresponding with 1 and 3–7 in the attached drawings, is substantially identical to that described hereinabove, while the emitted fluorescence is detected simultaneously by two independent cross-polarized detector channels, similar to 11 in the drawing, arranged facing each other on a line perpendicular to the direction of the excitation beam. In one of these channels the emitted light passes through a polarizer with the direction of polarization perpendicular to the plane of polarization of the exciting beam and in the other through a polarizer oriented parallel to that plane. This arrangement permits the use of a square sample cuvette and the direct reading or recording of the ratio $I_\parallel / I_\perp$, e.g. on a ratio digital volt meter. As stated above this ratio $I_\parallel / I_\perp$ can serve as a direct criterion for malignancy, as will be shown in the examples herein. In an instrument of this type there is of course no need to provide for the photodiode compensator 2.

An alternative type of apparatus permitting the direct reading of the ratio $I_\parallel / I_\perp$ would be one comprising a single detector channel (11 in the drawing) and two excitation channels similar to the one described above, each emitting polarized excitation light, the directions of the polarization in the two channels being perpendicular to each other. The sample is intermittently exposed to the one or the other of these two excitation beams, by means of a conventional chopping device, e.g. a sectored mirror, and the signal obtained from the photomultiplier 15 can be analyzed for its AC and DC components, permitting the direct reading of the ratio $I_\parallel / I_\perp$.

Using the above described method and apparatus to measure the fluorescence polarization of the DPH probe embedded in the lipid layer, a large number of determinations of $I_\parallel / I_\perp$ were made with mice lymphocytes, both normal and leukaemic. The ratio obtained for normal cells from different strains of mice at 25°C was always within the range of 1.75± 0.02 and was the same for normal lymphocytes taken from the lymph nodes, the thymus or the bone marrow of the mice. Against this, the ratios of $I_\parallel / I_\perp$ obtained with lymphoma cells of mice of the same strain infected with Ascites tumor were all in the range of 1.55±0.02. The derived microviscosities $\bar{\eta}$ at 25°C (in poise) were 2.8 and 1.6 for the normal lymphocytes and the lymphoma cells, respectively.

A similar difference was also observed in human lymphocytes and was applied for the detection of chronic lymphatic leukaemia and acute lymphoblastic leukaemia. It was found that the ratio $I_\parallel / I_\perp$ measured with normal lymphocytes obtained from the peripheral blood of normal donors was 1.86±0.03 (average of about 40 donors), while a value of 1.71±0.05 was measured with leukaemic cells taken from the peripheral blood of chronic lymphatic leukaemia patients (average of about 40 patients). The respective microviscosities at 25°C were calculated to be 3.7 poise for normal lymphocytes and 2.5 poise for leukaemic cells. Fluorescence polarization measurements were also carried out with leukaemic cells taken from the peripheral blood of acute lymphoblastic patients (4 cases). The $I_\parallel / I_\perp$ ratios measured were all about 1.67 and the microviscosity at 25°C about 2.2 poise.

The above described results, in particular their reproducibility and the comparatively narrow range of deviations, both with normal cells and with malignant ones, show the reliability of the method according to the invention for the detection of malignant transformations in mammalian cells. It should also be pointed out that in some cases of chronic lymphatic leukaemia patients the change in microviscosity of the lipid layer could be observed several months before the appearance of significant changes in the blood count. Furthermore, on one case of acute lymphoblastic leukaemia under study, the reduction in microviscosity of the lipid layer persisted even after the full remission of the acute leukaemia, as a consequence of treatment involving a large scale blood transfusion. The microviscosity remained at its low value even though the blood count and morphology appeared to be normal.

The major lipid parameter which determines fluidity (and thus controls the recorded degree of fluorescence polarization with DPH) is the ratio of cholesterol to phospholipids ("C/P ratio"), see Cogan et al., Biochemistry, 12, 521–528 (1970), R. A. Cooper, Semin. Hematol. vol. 7, 296–322 (1970) and Inbar and Shinitzky, Proc. Natl. Acad. Sci. U.S., 1974. The measurement with DPH provides thus a tool for indirect determinations in the measured system (intact cells, isolated membranes, lipid dispersion, sera). The C/P ratio is a subtle indicative of any disorders in lipid metabolism.

The invention is illustrated in the following non-limiting examples.

EXAMPLE 1

Normal lymphocites were collected from lymph nodes, thymus and bone marrow of adult mice, while malignant lymphoma cells were obtained from adult mice, 10 to 14 days after their intraperitoneal inoculation with about $10^5$ cells each of an Ascites form of a Moloney virus-induced lymphoma. For each experiment freshly collected normal lymphocites or lymphoma cells were washed three times with 0.15 M aqueous KCl solution and were suspended in 0.15 M-KCl solution.

used as a cut-off filter in the detector channel for wavelengths below 390 nm.

In all fluorescence measurements the temperature of the sample was controlled with a thermostatically controlled bath. The temperature of the sample was measured with a thermometer immersed in the analysed solution to an accuracy of 0.3°C. The DPH-labelled samples were exposed to the excitation light for less than 10 seconds in order to eliminate the possibility of reversible bleaching of the DPH. Before each measurement the cell suspensions were stirred gently to ensure isotropic distribution.

TABLE 1

Normal lymphocites and leukaemic cells from mice

| Cells | Strain | Organ | No. of samples tested | Fluorescence polarization of DPH at 25°C $I_{\parallel}/I_{\perp}$ | P | r | Micro-viscosity at 25°C $\bar{\eta}$ (poise) |
|---|---|---|---|---|---|---|---|
| Normal lymphocytes | A/J | Lymph-nodes | 17 | | | | |
| | | Thymus | 18 | | | | |
| | | Bone marrow | 25 | | | | |
| | $C_{57}Bl$ | Lymph-nodes | 15 | 1.75±0.02 | 0.273 | 0.200 | 2.8 |
| | | Thymus | 25 | | | | |
| | | Bone marrow | 14 | | | | |
| | $C_{57}Bl$ (nudes) | Lymph-nodes | 10 | | | | |
| Leukaemic cells | A/J | Ascites tumor | 163 | 1.55±0.2 | 0.216 | 0.160 | 1.6 |

An aqueous dispersion of DPH was prepared by blowing 0.1 ml of a $2 \times 10^{-3}$ M DPH solution in tetrahydrofuran into 100 ml of a vigorously stirred aqueous 0.15 M KCl solution. Stirring was continued for 15 minutes at 25°C, whereby a clear stble aqueous dispersion of $2 \times 10^{-6}$ M DPH was obtained which is practically void of fluorescence.

One volume of the cell suspension in 0.15 M aqueous KCl solution, obtained as described above (about $5 \times 10^6$ to $2.5 \times 10^7$ cells/ml) was mixed with one volume of the DPH dispersion and incubated at 25°C. The penetration of DPH into the cell membrane was followed by the steep increase in fluorescence intensity, which levelled off after about 60 minutes. The labelled cells were then washed twice with 0.15 M KCl solution, and immediately used for fluorescence measurements.

Fluorescence polarization and intensity were measured with an instrument such as described above. The sample was excited with a 366 nm band (generated by a 500 W mercury arc) which was passed through a Glan-air polarizer. A 2N sodium nitrite solution was

EXAMPLE 2

The procedure described in Example 1 was used for fluorescence polarization measurements of DPH-labelled normal lymphocytes isolated from the peripheral blood of normal human donors and of similarly stained leukaemic cells obtained from the peripheral blood of patients suffering from chronic lymphatic leukaemia and acute lymphoblastic leukaemia.

The results are shown in the following Table 2.

| Cells | Origin | No. of samples tested | Fluorescence polarization of DPH at 25°C $I_{\parallel}/I_{\perp}$ | P | r | Micro-viscosity at 25°C $\bar{\eta}$ (poise) |
|---|---|---|---|---|---|---|
| Normal lymphocytes | Peripheral blood of normal donors | 38 | 1.86±0.03 | 0.301 | 0.223 | 3.7 |
| Chronic lymphatic leukaemic cells | Peripheral blood of leukaemic patients | 38 | 1.71±0.05 | 0.261 | 0.191 | 2.5 |
| Acute lymphoblastic leukaemic cells | Peripheral blood of leukaemic patients | 4 | 1.67 | 0.250 | 0.182 | 2.2 |

Fluorescence polarization measurements with cell suspensions are susceptible to experimental errors that originate from scattering depolarization of the fluorescence and from penetration of background light into the emission channels. It was found, however, that when DPH is used as the fluorescence probe these errors can be easily determined or even eliminated. If the DPH-labelled cell suspensions are progressively diluted with 0.15 M aqueous KCl solution, a constant value of P is reached at concentrations of about $7 \times 10^6$ lymphocytes/ml and about $2 \times 10^{-6}$ lymphoma cells/ml. At these cell concentrations scattering depolarization of the fluorescence is therefore negligible, whereas the contribution of background light to the fluorescence signal, as checked with reference suspensions of unlabelled cells, was found to be less than 3 percent in all systems studied. Concentrations in the above mentioned range were therefore employed in most fluorescent measurements and no corrections were made for the contributions of scattering depolarization and background light to the measured values.

We claim:

1. A method of detecting in vitro abnormal behavior of mammalian cells comprising the steps of:
    isolating from a living body of a mammal, cells which it is desired to examine,
    exposing said cells to electromagnetic radiation in the range of from about 200 to about 700 nm thereby to cause an electromagnetic signal to emerge from the lipid layer of the surface membrane of said cells,
    measuring at least one parameter of said electromagnetic signal thereby to obtain an indication of the fluidity of said lipid layer,
    comparing said indication obtained in the measuring step with a corresponding indication obtained from normal cells of the same type,
    thereby to determine whether or not the fluidity of said lipid layer of said mammalian cells tested significantly differs from the corresponding value of said normal cells of the same type, a difference indicating abnormal behavior of said mammalian cells tested.

2. A method of detecting in vitro abnormal behaviour of mammalian cells which comprises introducing a hydrocarbon compatible fluorescent compound into the lipid layer of the cell membrane, exposing the thus labelled cells to polarized excitation radiation, measuring the fluorescence polarization of the radiation emitted from the sample and comparing the measurement thereby obtained with that of normal cells of the same type.

3. A method according to claim 2, wherein intact cells are used.

4. A method according to claim 2, wherein the fluorescence polarization is determined by measuring the fluorescence intensities $I_\parallel$ and $I_\perp$ after the fluorescence emission is passed through a polarizer having its direction of polarization parallel and perpendicular, respectively, to the direction of polarization of the exciting radiation, and deducing therefrom the value $I_\parallel / I_\perp$ which is compared with the corresponding value obtained from measurements of normal cells.

5. A method according to claim 4, wherein the ratio $I_\parallel / I_\perp$ is measured directly by the use of two detection channels having their directions of polarization perpendicular to each other.

6. A method according to claim 2, wherein the fluorescent compound used for labelling is a member selected from the group consisting of 1,6-diphenyl-1,3,5-hexatriene and lower alkyl derivatives thereof.

7. A method according to claim 2, wherein the cells to be measured are labelled by mixing a suspension of the cells with an aqueous dispersion of the fluorescent compound and incubating the mixture.

8. A method in accordance with claim 4, wherein the ratio $I/I$ is measured directly by the use of two alternating excitation channels having their directions of polarization perpendicular to each other.

* * * * *